United States Patent
Uster et al.

(10) Patent No.: US 6,818,227 B1
(45) Date of Patent: Nov. 16, 2004

(54) LIPOSOME COMPOSITION AND METHOD FOR ADMINISTRATION OF A RADIOSENSITIZER

(75) Inventors: Paul S. Uster, Tracy, CA (US); Adam A. Zetter, Menlo Park, CA (US); Kristen M. Hjortsvang, Fremont, CA (US); James L. Slater, Palo Alto, CA (US); George Z. Zhu, San Jose, CA (US)

(73) Assignee: Alza Corporation, Mountain View, CA (US)

( * ) Notice: Subject to any disclaimer, the term of this patent is extended or adjusted under 35 U.S.C. 154(b) by 0 days.

(21) Appl. No.: 09/498,704

(22) Filed: Feb. 7, 2000

Related U.S. Application Data
(60) Provisional application No. 60/119,272, filed on Feb. 8, 1999.

(51) Int. Cl.[7] .............................................. A61K 9/127
(52) U.S. Cl. .................. 424/450; 424/1.21; 424/9.321; 424/9.51; 264/4.1; 264/4.3
(58) Field of Search ................................ 424/450, 1.21, 424/9.321, 9.51; 264/4.1, 4.3, 4.6; 456/829

(56) References Cited

U.S. PATENT DOCUMENTS

| | | | |
|---|---|---|---|
| 4,942,226 A | | 7/1990 | Saari |
| 5,077,034 A | | 12/1991 | Kassis et al. |
| 5,213,804 A | * | 5/1993 | Martin |
| 5,223,263 A | | 6/1993 | Hostetler et al. |
| 5,728,684 A | | 3/1998 | Cheng et al. |
| 5,811,073 A | | 9/1998 | Kassis et al. |

FOREIGN PATENT DOCUMENTS

| | | |
|---|---|---|
| JP | 5058879 A | 3/1993 |
| WO | 95/15154 | 6/1995 |
| WO | WO 96/25147 | 8/1996 |
| WO | WO 96 25147 A | 8/1996 |
| WO | WO 99/30561 | 6/1999 |
| WO | WO 99 30561 A | 6/1999 |
| WO | WO 00/43045 | 7/2000 |
| WO | WO 00 43045 A | 7/2000 |

OTHER PUBLICATIONS

Harrington et al., "Stealth Liposome Encapsulated Iododeoxyuridine (SLIUDR) for Targeted Radiosensitisatin in Xenograft Tumours," British J. of Cancer, p. 35, V.78(2), May, 1998.

Harrington, K., et al., "Stealth liposome encapsulated iododeoxyuridine (SLIUdR) for targeted radiosensitisation in xenograft tumours" British Journal of Cancer vol. 78 suppl. 2 pp. 35 abstract# P28 (1998).

Atcher, R.W., et al., "Halogenated Pyrimidines as Radiosensitizers for High–LET Radiation" Radiation Research 117:351–355 (1989).

Epstein, A.H., et al., "Tumour Radiosensitization with the Halogenated Pyrimidines 5'–bromo– and 5'–iododeoxyuridine" BJR Supplement 24:209–214 (1992).

Goodman and Gilman's The Pharmacological Basis of Therapeutics, Ninth Edition, Hardman, et al. (eds), McGraw–Hill, New York, pp. 1247–1248 (1996).

Hofer, K.G., "Nouvelles Et Travaux" Bull Cancer (Paris) 67(3):343–353 (1980).

(List continued on next page.)

Primary Examiner—Gollamudi S. Kishore (57) ABSTRACT

A method for administering a radiosensitizer to a tumor site in a subject is described. The method includes preparing liposomes composed of a vesicle-forming lipid and a lipid-derivatized radiosensitizer. In one embodiment, the radiosensitizer is dipalmitoyl-5-iodo-2'-deoxyuridine. A method for preparing the liposome composition including the lipid-derivatized radiosensitizer is also disclosed.

21 Claims, 3 Drawing Sheets

OTHER PUBLICATIONS

Mori, A., et al., "Immunotargeting of Liposomes COntaining Lipophilic Antitumor Prodrugs" *Pharmaceutical Research* 10(4):507–514 (1993).

Mori, A., et al., "Characterization of Organ–specific Immunoliposomes for Delivery of 3',5'-o-dipalmitoyl-5-fluoro-2'-deoxyuridine in a mouse lung-metastasis model" *Cancer Chemother Pharmacol* 35:447–456 (1995).

Scherphof, G.L., et al., "Lipid Flow Phenomena Between Liposomes, Lipoproteins and Cell Membranes; Applications in Drug Delivery" *Liposome Dematics*, Braun-Falco, Korting and Maibach (eds), Springer Verlag: Berlin, pp. 11–19 (1992).

Scherphof, G.L., et al., "Liposomes in Chemo– and Immunotherapy of Cancer" *Lipids* 22(11):891–896 (1987).

Schwendener, R.A., et al., "5'-O-Palmitoyl- and 3', 5'-0-Dipalmitoyl-5-Fluoro-2'-Deoxyuridine—Novel Lipophilic Analogues of 5'-Fluoro-2'-Deoxyuridine: Synthesis, Incorporation into Liposomes and Preliminary Biological Results" *Biochemcal and Biophysical Research Communication* 126(2):660–666 (1985).

Schwendener, R.A., "The Preparation of Large Volumes of Homogeneous, Sterile Liposomes Containing Various lIpophilic Cytostatic Drugs by the Use of a Capillary Dialyzer" *Cancer Drug Delivery* 3(2):123–129 (1986).

Shenoy, M.A. and Singh, B.B., "Chemical Radiosensitizers in Cancer Therapy" *Cancer Investigation* 10(06):533–551 (1992).

Smolin, G., et al., "Idoxuridine-Liposome Therapy for Herpes Simplex Keratitis" *American Journal of Ophthalmology* 91:220–225 (1981).

Supersaxo, A., et al., "The Antitumour Effect of Lipophilic Derivatives of 5-fluoro-2'-deoxyuridine Incorporated into Liposomes" *J microencapsulation* 5(1):1–11 (1988).

Van Borssum Waalkes, M., et al., "In–vitro Stability and Cytostatic Activity of Liposomal Formulations of 5-fluoro-2'-deoxyuridine and its Diacylated Derivatives" *Biochimica et Biophysica Acta* 1148:161–172 (1993).

Van Borssum Waalkes, M., et al., "In vivo Distribution and Antitumor Activity of Liposomal 3', 5'-O-dipalmitoyl-5-fluoro-2'-deoxyuridine" *J Microencapsulation* 9(3):335–346 (1992).

Van Borssum Wallkes, M., *Lipophilic Derivatives of 5-Fluoro-2'-Deoxyuridine as Liposomal Anticancer Agents* pp. 7–159 (1992).

Van Borssum Waalkes, M. and Scherphof, G.L., "Liposome–Incorporated 3', 5'-O-Dipalmitoyl-5-Fluoro-2'-Deoxyuridine as a Slow–Release Anti-Tumor Drug Depot in Rat Liver Macrophages" *Selective Cancer Therapeutics* 6(1):15–22 (1990).

Van Borsum Waalkes, M., et al., "Toxicity of Liposomal 3'-5'-O-dipalmityole-5-fluoro-2'-deoxyuridine in Mice" *Anti-Cancer Drug Design* 13:291–305 (1998).

Atsuhide Mori, et al., "Immunotargeting of Liposomes Containing Lipophilic Antitumor Prodrugs," Pharmaceutical Research Article, 4th ed., Plenum Publishing Corporation (USA), vol. 10 (No. 4), p. 507–514, (Oct. 23, 1993).

* cited by examiner

LIPOSOME COMPOSITION AND METHOD FOR ADMINISTRATION OF A RADIOSENSITIZER

This application claims priority of provisional application No. 60/119,272 filed Feb. 8, 1999, now pending, which is incorporated herewith by reference.

FIELD OF THE INVENTION

The present invention relates to a composition and method for administration of a radiosensitizer to enhance radiation treatment as a part of cancer therapy.

BACKGROUND OF THE INVENTION

Radiation treatment has become a conventional part of cancer therapy. One shortcoming to radiotherapy, however, is the destruction to normal, healthy tissue surrounding the tumor which occurs during treatment. Another shortcoming is that after cessation of treatment, recurrence of the tumor can and does occur. Recurrence of the tumor has been partly attributed to the presence of radioresistant hypoxic tumor cells, and the enhancement of radiation dose to damage the hypoxic tumor tissue is often necessary. However, to save normal, healthy tissue, a reduction in the total radiation dose would be desirable. Obviously, these two factors are contradictory. Therefore, the use of certain drugs and chemicals that preferentially sensitize hypoxic tumor cells to radiation, radiosensitizers, are employed.

Radiosensitizers are chemical agents that have the capacity to increase the lethal effects of radiation when administered in conjunction with radiation and there are a variety of radiosensitizers that act by more than one mechanism. One class of radiosensitizers that directly alter the macromolecular apparatus determining the radiosensitivity are halogenated pyrimidines. The halogenated pyrimidines include 5-chlorodeoxy-uridine (CudR), 5-bromodeoxyuridine (BudR) and 5-iododeoxy-uridine (IudR). These radiosensitizers are incorporated into the DNA in the tumor cell in place of thymine and render the cell more susceptible to inactivation by radiation.

In cancer radiotherapy, the usefulness of inducing an increase in radiosensitivity by selective incorporation of a halogenated pyrimidine is limited by several factors. First, the drug must be present for a period long enough to allow the cells to pass through at least one DNA synthesis cycle since halogenated pyrimidines are incorporated only in cells in the S phase. While tumor cells often multiply faster than normal tissues, the fact that certain tumors may have doubling times varying from days to weeks complicates the planning of therapy. Second, the degree of radiosensitization is directly related to the degree of thymidine substitution. Hence, only a prolonged infusion of the drug in free form will maximize its incorporation. Third, it is not only the extent of sensitization that is important, but rather the total number of cells that must be sensitized to obtain any significant effect on the tumor. Fourth, the rapid hepatic degradation and dehalogentaion must be overcome.

One approach to overcoming some of these limitations has been to encapsulate the halogenated pyrimidine in liposomes. However, these attempts have not been entirely satisfactory because the radiosensitizers tend to leak out of the liposomes rapidly and the liposomes have poor stability in serum.

SUMMARY OF THE INVENTION

Accordingly, it is an object of the invention to provide a composition and method for administration of a radiosensitizer for radiotherapy.

It is a further object of the invention to provide a method for achieving radiosensitization of a tumor with a single, weekly dose.

It is a further object of the invention to provide a composition which achieves a two-fold higher distribution of the radiosensitizer in the tumor tissue than in the normal, healthy tissue.

In one aspect, the invention includes a method for administering a radiosensitizer to a tumor. The method includes preparing liposomes comprised of (i) a vesicle-forming lipid; (ii) between 1–20 mole percent of a vesicle-forming lipid derivatized with a hydrophilic polymer chain, and (iii) between 1–15 mole percent of a radiosensitizer derivatized with a lipid moiety linked to the radiosensitizer; and administering the liposomes to a tumor-bearing patient.

In one embodiment, the radiosensitizer is 5-iodo-2'deoxyuridine or 5-bromo-2'deoxyuridine.

In another embodiment, the lipid moiety is a fatty acid or a saturated fatty acid. In other embodiments, the lipid moiety is selected from lauric acid, myristic acid, palmitic acid, stearic acid, arachidic acid, behenic acid and lignoceric acid.

In a preferred embodiment, the radiosensitizer is 5-iodo-2'-deoxyuridine and the lipid moiety is palmitic acid.

The radiosensitizer is derivatized with a second lipid moiety, in another embodiment of the invention. For example, the radiosensitizer is 5-iodo-21-deoxyuridine and the lipid moieties are palmitic acid.

The hydrophilic polymer chain included in the lipid composition and derivatized to a lipid moiety, in one embodiment, is polyethyleneglycol.

In another aspect, the invention includes a method for preparing a liposome composition including a radiosensitizer, by mixing in a lipid solvent (i) a vesicle-forming lipid; (ii) between 1–20 mole percent of a vesicle-forming lipid derivatized with a hydrophilic polymer chain, and (iii) between 1–15 mole percent of a radiosensitizer derivatized with a lipid moiety linked to the radiosensitizer; and adding an amount of a second solvent selected (i) to achieve a lipid solvent amount greater than 10 weight percent and less than about 50 weight percent and (ii) to obtain a liposome size less than that obtained at another lipid solvent amount, where the lipid solvent and the second solvent are miscible in the resulting hydration mixture.

In one embodiment, the lipid solvent is an alcohol, such as methanol, ethanol or butanol. The second solvent, in one embodiment, is water.

In another aspect, the invention includes a liposome composition for administration of a radiosensitizer. The composition includes liposomes comprised of (i) a vesicle-forming lipid; (ii) between 1–20 mole percent of a vesicle-forming lipid derivatized with a hydrophilic polymer chain, and (iii) between 1–15 mole percent of a radiosensitizer derivatized with a lipid moiety linked to the radiosensitizer. The composition is formed by (a) mixing components (i), (ii) and (iii) in a lipid solvent; and (b) adding a selected amount of a second solvent, said selected amount effective (i) to achieve a lipid solvent amount greater than 10 weight percent and less than about 50 weight percent and (ii) to obtain a liposome size smaller than that obtained a lipid solvent amount other than said selected amount, said lipid solvent and said second solvent being miscible at the selected amount of second solvent.

These and other objects and features of the invention will be more fully appreciated when the following detailed description of the invention is read in conjunction with the accompanying drawings.

DETAILED DESCRIPTION OF THE INVENTION

I. Definitions

As used herein, "dpIUdR" refers to 3',5'-dipalmitoyl-5-iodo-2'-deoxyuridine.

As used herein, "IUdR" refers to 5-iodo-2'-deoxyuridine.

II. Lipid Derivatized Radiosensitizer

As discussed above, radiation sensitizers are compounds that are capable of being incorporated into cellular DNA and subsequently enhancing the damage caused by ionizing radiation when solid tumors are treated with radiation therapy. Two such radiation sensitizers contemplated for use in the present invention are 5-iododeoxyuridine and 5-bromodeoxyuridine. These compounds behave as an analog of thymidine and in the cell undergo phosphorylation and ultimate incorporation into DNA in place of thymidylate.

In the present invention the radiosensitizer is derivatized with a lipid moiety for incorporation into the lipid bilayer of a liposome. A wide variety of lipid moieties are suitable for incorporation into a liposome lipid bilayer and include fatty acids, monoacylglycerols, diacylglycerols, fatty alcohols, cholesterol, and phospholipids. These lipids are merely exemplary, and it will be appreciated that any compound which when derivatized to the radiosensitizer renders the radiosensitizer more lipophilic is suitable. In a preferred embodiment, the radiosensitizer is derivatized with a fatty acid, which in preferred embodiments has between 2–24 carbon atoms, more preferably between 10–20 carbon atoms. Suitable fatty acids include saturated fatty acids such as lauric acid (C12), myristic acid (C14), palmitic acid (C16), stearic acid (C18), arachidic acid (C20), behenic acid (C22), lignoceric acid (C24) and unsaturated fatty acids, such as oleic acid (c18).

It will be appreciated by those of skill in the liposome art that the length of the acyl tail on the lipid moiety is selected according to the degree of compatibility desired with the vesicle-forming lipids forming the liposome lipid bilayer. Lipid moieties having an acyl chain length within one or two carbons of the length of the acyl chain on the vesicle-forming lipid will result in a more uniform lipid bilayer with the derivatized radiosensitizer more strongly retained. This feature can be used to tailor release of the derivatized radiosensitizer from the bilayer, if desired.

The radiosensitizer can be derivatized with one lipid moiety, or in a preferred embodiment of the invention, with two lipid moieties. More lipid moieties may also be possible in some situations. The position at which the radiosensitizer is derivatized is variable, with the proviso that the compound must retain therapeutic activity after release from the lipid derivative or, in the cases where the lipid derivative is retained, the therapeutic activity is retained when in the derivatized form.

Figure 1:
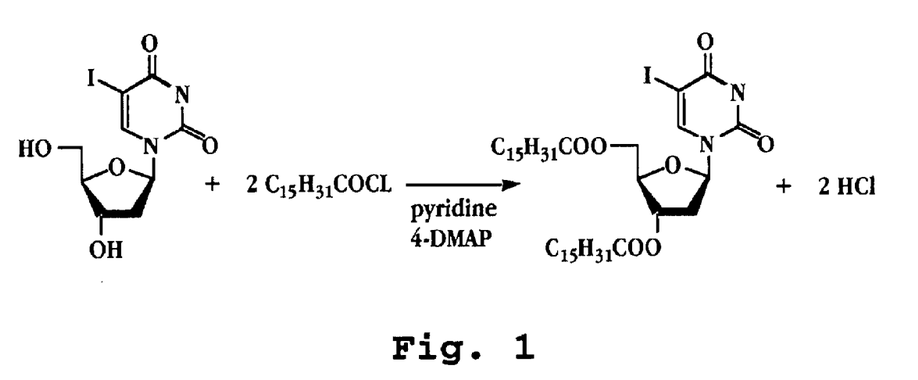
FIG. 1 is a synthetic reaction scheme for synthesis of 3',5'-dipalmitoyl-5-iodo-2'-deoxyuridine.

In studies performed in support of the invention, 5-iodo-2'deoxyuridine, referred to herein as IUdR, was derivatized with a 16-carbon fatty acid, palmitic acid, at two positions on the ribose sugar of IUdR, as shown in FIG. 1. In the reaction scheme shown in the figure and detailed in Example 1, IUdR was reacted with a small excess of palmityl chloride and 4-dimethylpyridine catalyst in pyridine or in pyridine/chloroform as the solvent to yield 3',5'-dipalmitoyl-5-iodo-2'-deoxyuridine, referred to herein as dpIUdR. As will be described below, the dpIUdR was incorporated into liposomes and tested in vivo for therapeutic efficacy as a radiosensitizer.

III. Method of Preparing the Liposome Composition

In one aspect, the invention includes a method of preparing a liposome composition suitable for use in administering a lipid-derivatized radiosensitizer, as exemplified by dpIUdR. One feature of therapeutic liposome compositions is the drug/lipid ratio, where a high drug/lipid ratio is preferred to achieve a therapeutic efficacy with as low of a lipid burden to the patient as possible. Preparation of a lipid-derivatized compound poses formulation issues not encountered with conventional, non-lipid derivatized compounds since the lipid tail on the compound contributes to the lipid bilayer and the total lipid content. As the total lipid content increases, sizing of the liposomes by conventional techniques, such as extrusion through polycarbonate membranes, becomes difficult and limits the drug/lipid ratio which can be obtained.

This point is illustrated by the data set forth in Table 1. Liposomes were prepared according to the procedure set forth in Example 2, where the lipids hydrogenated soy phosphatidyl choline (HSPC) and methoxy-polyethylenelglycol-distearyl-phosphatidyl-ethanolamine (mPEG-DSPE) and the lipid-derivatized dpIUdR were dissolved in ethanol in molar ratios of 89/5/6, 87.5/5/7.5 and 85/5/10. The ethanol-lipid solutions were hydrated with an aqueous second solvent to a final ethanol amount of 10.1 weight percent. The liposome suspensions were extruded through polycarbonate disc membranes to achieve a target liposome size of about 100 nm. The liposome particle size in each suspension was then measured using quasi-elastic light scattering and the results are shown in Table 1.

As seen in Table 1, liposomes prepared with 6 and 7.5 mole percent dpIUdR could be sized by extrusion through the membranes. However, at 10 mole percent dpIUdR, the target liposome size of around 100 nm could not be achieved, as the liposomes could no longer be readily extruded at the higher lipid content.

TABLE 1

| Mole % dpIUdR | Conc. dpIUdR (mg/ml) | Drug/lipid ratio (mol/mol) | liposome size after extrusion (nm) |
|---|---|---|---|
| 6 | 2.35 | 0.06 | 90 |
| 6 | 3.48 | 0.06 | 120 |
| 7.5 | 2.06 | 0.08 | 102 |
| 10 | 3.37 | 0.10 | 143 |

This problem of liposome sizing at higher loading of a lipid-derivatized drug was overcome by preparing the liposomes according to a method now to be described. The method provides a means to achieve a high drug/lipid ratio while retaining the ability to obtain the desired liposome size, either through use of the method alone or in combination with a second sizing step such as extrusion.

In the method, the vesicle-forming lipid and the lipid-derivatized compound are mixed in a lipid solvent. As used herein, "lipid solvent" refers to an organic solvent in which the lipid components of the liposome are soluble, at any temperature. Exemplary lipid solvents include alcohols, such as methanol, ethanol, butanol, etc. and low molecular weight polyols, such as glycerol, propyleneglycol and ethyleneglycol. The lipids are added to the solvent in the desired molar ratio and mixed until dissolved, with heating as necessary. An amount of a second solvent is then added to the lipid solvent/lipid mixture to form a hydration mixture. The second solvent, as used herein, refers to a solvent that is miscible with the lipid solvent in some proportion, and must be miscible with the lipid solvent in the resulting hydration mixture. The second solvent is added to the lipid solvent mixture in an amount sufficient to bring the weight percentage of the lipid solvent to a selected point which is greater than about 10 weight percent but less than about 50 weight percent of the lipid solvent, more preferably to a lipid solvent concentration in the range of 15–45 weight percent, most preferably to a lipid solvent concentration in the range of 20–40 weight percent, to obtain liposomes having a desired size, as will now be illustrated.

Figure 3:
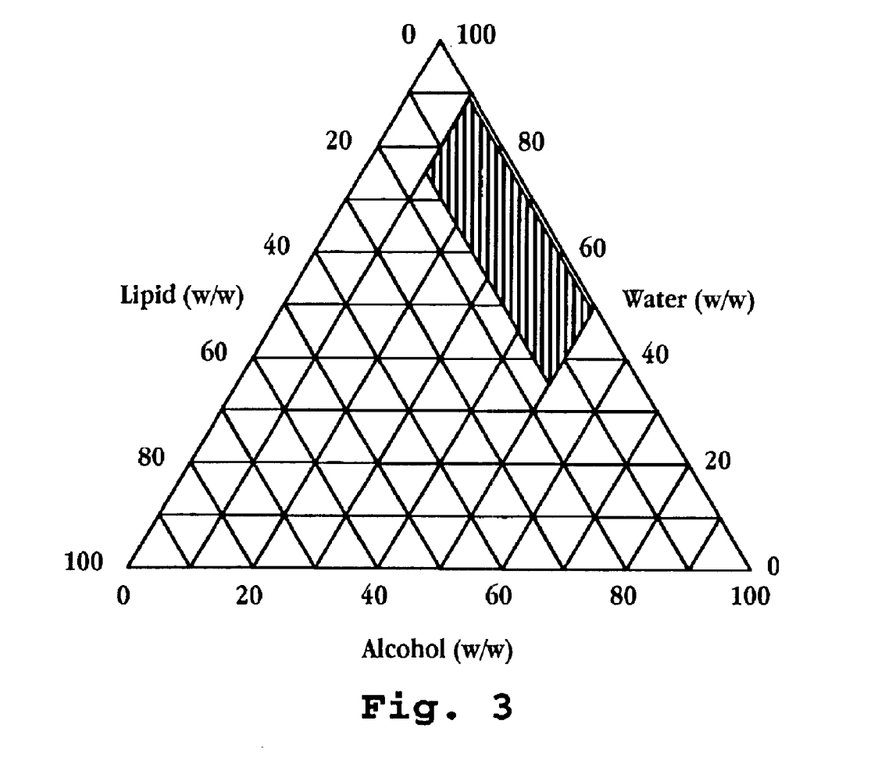
FIG. 3 is a phase diagram for a lipid, solvent, second solvent mixture, showing a preferred operating region when the solvent is ethanol and the second solvent is water.

As described in Example 3, the lipids HSPC, MPEG-DSPE and dpIUdR were dissolved in ethanol in an 89:5:6 molar ratio. This lipid stock solution was used to prepare liposome suspensions by hydrating an amount of the lipid solution with a second solvent, an aqueous buffer. Liposome suspensions were prepared in triplicate at final ethanol weight percentages of 8.1, 10.1, 12.2, 14.3, 16.5, 20.8, 25.3, and 44.1. The average size of the liposomes in each sample was measured by quasi-elastic light scattering, and the results are shown in Table 2.

invention. In the diagram, the shaded region corresponds to formation of liposomes where the lipid solvent amount is between about 10–50 weight percent and the weight percent of the lipids is between 0.1–15. Depending on the lipid mixture and the lipid solvent, the point at which a minimum in liposome particle size occurs within the operating region can be determined. The liposome suspensions in the operating region are visually clear and contain submicron size liposomes. It will be appreciated that the operating region will vary slightly according to the lipid, solvent and drug components. One of skill in the art can readily conduct a study like that set forth in Example 3 and in Table 2 to determine the amount of lipid solvent that yields a minimum in the liposome size.

Liposomes formed by the above-described method can be, depending on the lipid solvent amount in the hydration mixture, at a minimum particle size. Thus, in some cases, it may not be necessary to further size the liposomes via extrusion or other technique. In some cases, it may be desirable to further process the liposomes, for example by extrusion. The method of preparation is particularly useful for incorporation of lipid-derivatized drugs into liposomes at a high drug-to-lipid ratio, where obtaining a pharmaceutically useful particle size of between 90–150 nm is difficult due to an inability to extrude the mixture, as discussed above. Formation of liposomes according to the invention overcomes this limitation, since the liposomes are at or near to the desired particle size upon hydration with the second solvent, and any further size processing is minimized. Thus, a higher lipid-derivatized drug load can be employed while still being able to achieve the desired liposome size.

This feature of the invention is illustrated by the study described in Example 4. Liposomes were prepared using the lipids HSPC, mPEG-DSPE and dpIUdR, where the molar amounts of the formulations were 89/5/6, 85/5/10, 80/5/15, 70/5/25 and 55/5/40. The lipids, including the dpIUdR, were dissolved in ethanol and then hydrated with sufficient water to bring the ethanol concentration in each mixture to 16.5

TABLE 2

| Sample No. | Liposome Size in nm at Weight Percent Ethanol | | | | | | | |
|---|---|---|---|---|---|---|---|---|
| | 8.1 | 10.1 | 12.2 | 14.3 | 16.5 | 20.8 | 25.3 | 44.1 |
| 1 | 51200 | 1410 | 226 | 197 | 84 | 53700 | 1000000 | 12500 |
| 2 | 71 | 46 | 78 | 119 | 149 | 27300 | 11000 | 10500 |
| 3 | 405 | 78 | 157 | 1360 | 84 | 11400 | 21400 | 12500 |
| AVERAGE | 17225 | 511 | 154 | 559 | 106 | 30800 | 344133 | 11833 |

Figure 2:
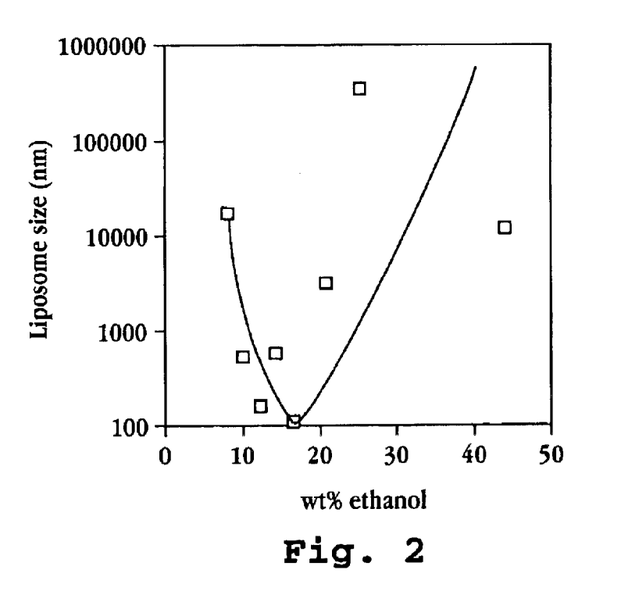
FIG. 2 is a plot of liposome size, in nm, as a function of weight percent ethanol during hydration of the liposome lipids.

In viewing the last row of Table 2, it is apparent that there is a minimum in the liposome particle size at 16.5 weight percent ethanol. This data is shown graphically in FIG. 2 and the trough in liposome size beginning at about 10 weight percent and ending at about 25 weight percent is apparent. A profile such as the one in FIG. 2 of lipid size as a function of ethanol content can be employed to determine the ethanol amount needed to obtain a particular liposome size. For example, the minimum particle size of 106 nm is obtained by hydrating the lipid-ethanol mixture to 16.5 weight percent ethanol. A larger particle size is obtained by hydrating to achieve more or less ethanol, according to the profile. Establishing such a profile, the target amount of lipid solvent to achieve a minimum particle size or a selected particle size is determined for any mixture of lipids and solvents, as will be further illustrated below.

FIG. 3 is a phase diagram showing the operating region for formation of the liposomes in accordance with the weight percent (20 volume percent). Each liposome suspension was then extruded as described in the Example and after extrusion, the average particle size of the liposomes in each suspension was measured. The results are shown in Table 3.

TABLE 3

| Mole percent dpIUdR | Conc,. dpIUdR (mg/ml) | Drug/lipid ratio (mol/mol) | Liposome size (nm) |
|---|---|---|---|
| 6 | 1.25 | 0.06 | 99 |
| 10 | 2.32 | 0.11 | 95 |
| 15 | 4.09 | 0.18 | 103 |
| 25 | 6.90 | 0.33 | 142 |
| 40 | — | 0.67 | —* |

*composition could not be extruded

Liposomes containing 6, 10 and 15 mole percent dpIUdR were readily sized to about 100 nm when prepared according to the method of the invention by hydrating the lipid mixture to an amount of lipid solvent that gives a minimum particle size. Importantly, the liposomes are formed at the minimum particle size with a molar drug-to-lipid ratio of between about 0.06–0.67. In a preferred embodiment of the invention, liposomes having the desired particle size are prepared using the method to a molar drug-to-lipid ratio of greater than about 0.18, as achieved with the liposome composition having 15 mole percent dpIUdR.

It will be appreciated that a variety of lipids are suitable for use in the present invention. The studies performed in support of the invention using HSPC and mPEG-DSPE are merely illustrative, and any of the vesicle-forming lipids known to those of skill in the field of liposomes are contemplated.

It is also possible to provide a targeted liposome composition containing the entrapped radiosensitizer, by including targeting moieties such as antibodies, to the distal ends of the PEG chains or on the outer surface of the liposomes, as is known in the art.

IV. Method of Administering the Composition

Liposomes prepared according to the invention and including dpIUdR were administered to animals to determine its effectiveness of the liposome composition as a radiosensitizer. The liposome formulation was composed of HSPC, mPEG-DSPE and dpIUdR in a molar ratio of 89:5:6. The liposome particle diameter was approximately 100 nm, with the dpIUdR prodrug incorporated into the liposome lipid bilayer by insertion of the palmitic acid chains into the bilayer. After delivery of the liposome vehicle to a tumor, hydrolysis of the prodrug releases IUDR into the tumor interstitial space where it can enter the cells and become incorporated into the DNA.

The radiosensitizing potential of the dpIUdR liposomes was evaluated in two murine tumor models, the RIF-1 fibrosarcoma model and the human head-and-neck xenograft KB tumor in nude mice. In the fibrosarcoma model, the animals were inoculated with the tumor and were used in the study after the tumor volume was greater than about 100 $mm^3$. The tumor-bearing animals were treated according to one of several regimens set forth in Table 4.

TABLE 4

| Regimen | Liposome Dose | Radiation Dose | Days of liposome Dose Administration[1] |
|---|---|---|---|
| 1 | 0.5 ml | None | −1, +2 |
| 2 | 0.5 ml | 5 × 4 Gy | −1, +2 |
| 3 | 1 ml | None | −1, +2 |
| 4 | 1 ml | 5 × 4 Gy | −1, +2 |
| 5 | 0.5 ml | 5 × 4 Gy | −3, 0 |
| 6 | 1 ml | 5 × 4 Gy | −3, 0 |
| 7 | none | 5 × 4 Gy | na |
| 8 (saline control) | none | None | none |

Figure 4:
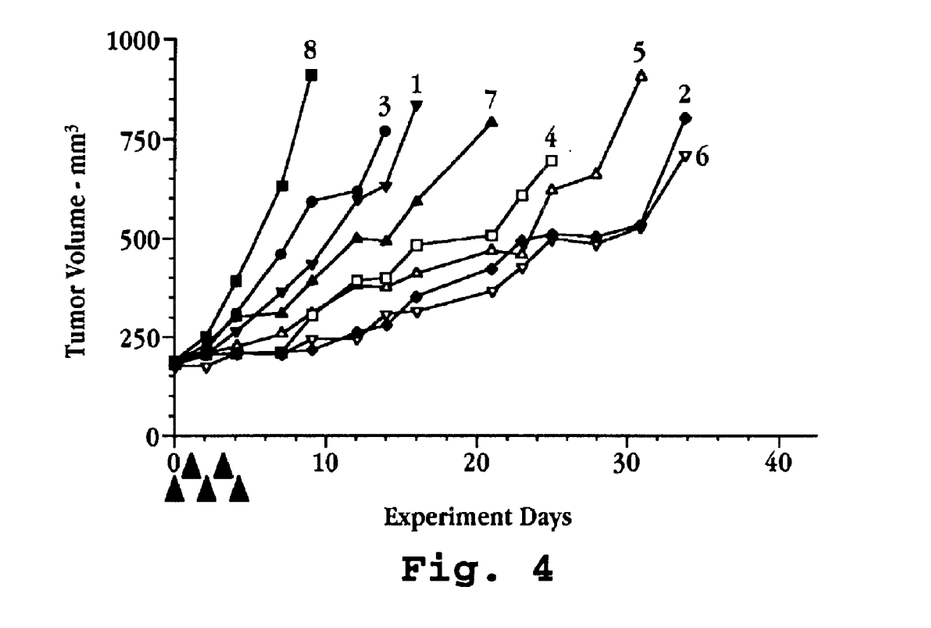
FIG. 4 is a plot showing tumor volume, in $mm^3$, for mice bearing firbrosarcoma tumors and treated with radiation alone (#7, closed triangles), with 0.5 ml (#1, closed, inverted triangles) or 1 ml (#3, closed circles) of dpIUdR-entrapped liposomes, and with dpIUdR liposomes at various dosages in combination with radiation (#2, 4, 5, 6)

The results of animals treated with regimens 1–8 of Table 4 are shown in FIG. 4. In the figure, the arrow heads along the x-axis on days 1–5 indicate the days on which a radiation treatment of 4 Gy was given. The data shows that treatment with dpIUdR containing liposomes and radiotherapy (regimens 2 (closed diamonds), 4 (open squares), 5 (open triangles), 6 (open inverted triangles) delays the growth of the tumor by as much as 30% over the same time period when compared to radiation alone (closed triangles). The data further shows that dosing one day prior to radiation therapy is sufficient for the dpIUdR to reach the tumor site and become incorporated into the tumor cell DNA, as evidenced by regimen 2 where the 0.5 ml liposome dose was administered just one day prior to the first radiation treatment and then on day 2 of the study.

In the KB tumor model study, the animals were dosed concurrent with initiation of radiation therapy. The tumor-bearing animals were divided into two test groups, one group receiving radiation therapy alone (9 Gy in 3 fractions) and the other group receiving a dose of the liposome composition on day zero, e.g., the day of radiation therapy. The group receiving the liposome composition also received a radiation treatment of 9 Gy in 3 fractions.

Figure 5A:
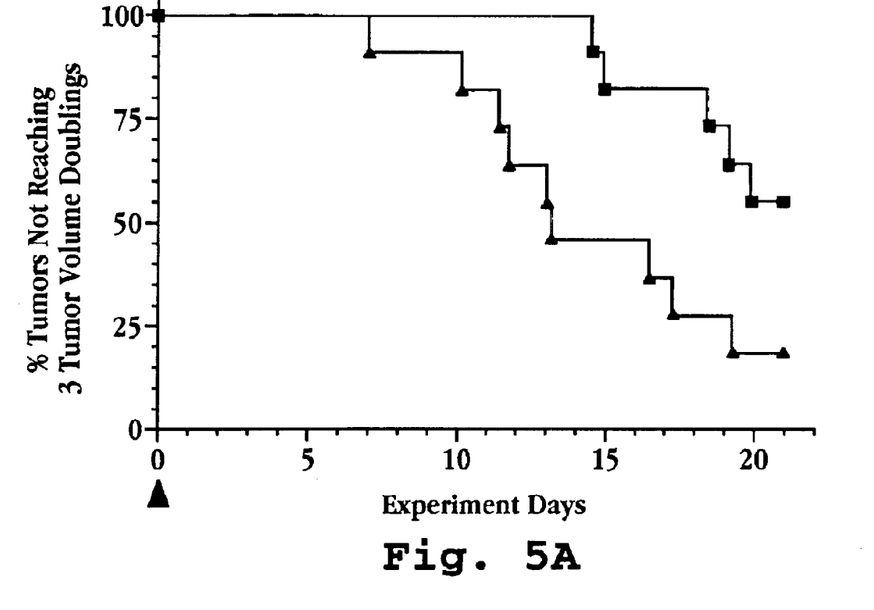
FIGS. 5A–5B are plots showing survival of tumor-bearing mice (FIG. 5A) and percentage change in tumor volume (FIG. 5B) following treatment with radiation alone (solid triangles) or with combined therapy of liposome-entrapped dpIUdR and radiation (solid squares).
Figure 5B:
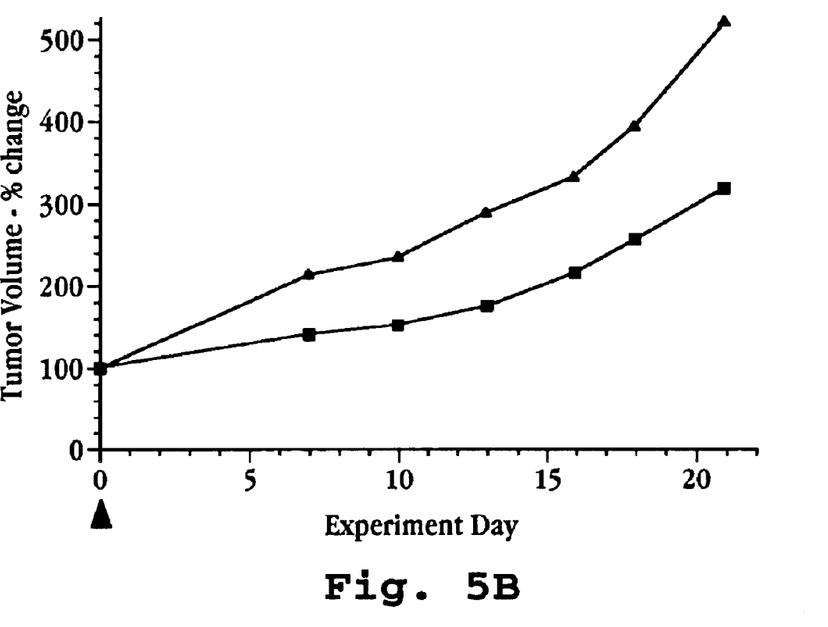

The results of the KB tumor model study are shown in FIGS. 5A–5B, where FIG. 5A shows the survival of KB-tumor bearing mice, taken as the percentage of tumors not reaching three tumor volume doublings as a function of number of days into the study. The data shows that when using dpIUdR in combination with radiation, the number of mice surviving three weeks after treatment is about 35% greater than the mice that were treated with radiation alone.

FIG. 5B shows the percentage change in tumor volume for the test mice, and indicated that dpIUdR in combination with radiation significantly delays tumor growth. At 20 days, the tumor growth of the group receiving radiation alone was more than 200% greater than the tumors of those receiving the combination treatment.

The liposomes of the invention containing the radiosensitizer are administered to patients by any of the known procedures utilized for administering liposomes. The liposomes can be administered intravenously, intraperitoneally, intramuscularly, intratumorally, or subcutaneously as a buffered, aqueous solution. Any pharmaceutically acceptable aqueous buffered or other vehicle can be utilized as long as the liposome structure and activity are retained.

The dosage for a mammal, including a human, will vary depending on the tumor type, tumor stage, and condition of the patient. Dosage levels for radionucleotides are well established and serve as a guideline for determining the dosage required for the liposome composition of the invention. In a preferred embodiment of the invention, the liposome composition is administered once or twice per week prior or during radiation therapy. In another preferred embodiment of the invention, the liposome composition is effective to achieve a two-fold higher distribution into the tumor tissue than in normal tissue.

V. EXAMPLES

The following examples illustrate the compositions and in methods of the invention and in no way are intended to be limiting.

Materials: The following materials were obtained from the indicated source: partially hydrogenated soy phosphatidylcholine (Vernon Walden Inc., Green Village, N.J.); cholesterol (Solvay Pharmaceuticals, The Netherlands); ethanol (Quantum Chemical Co. Tuscola, Ill.) and histidine (Seltzer Chemicals, Carlsbad, Calif.). mPEG-DSPE was prepared as described in the literature (for example, Zalipsky, S., et al, *Bioconjugate Chem.,* 4:296–299 (1993)).

Methods

QUELS: quasi-elastic light scattering was performed using a Brookhaven Instruments Model B1-200SM (Brookhaven Instruments Corporation, Holtsville, N.Y.).

Example 1

Synthesis of 3′,5′-dipalmitoyl-5-iodo-2′-deoxyuridine

Palmityl chloride was added slowly to a solution of deoxyuridine in pyridine or in pyridine/chloroform and 4-dimethylpyridine as a catalyst. The solution was mixed until yellow in color and then left to stand overnight for precipitation. The mixture was dissolved in chloroform and washed with 10% aqueous citric acid solution and saturated sodium bicarbonate solution. The chloroform was removed and methanol was added to yield a white precipitate, identified as 3',5'-dipalmitoyl-5-iodo-2'-deoxyuridine (66% yield). The synthetic reaction scheme is shown in FIG. 1.

Example 2

Conventional Liposome Preparation

The lipids hydrogenated soy phosphatidyl choline (HSPC) and distearoylphosphatidylcholine derivatized with methoxy-polyethyleneglycol (DSPE-mPEG) and dpIUdR in molar ratios of 89/5/6, 87.5/5/7.5 and 85/5/10 were each dissolved in ethanol at 70° C. until complete dissolution was achieved (about 1 hour). The lipid mixtures were hydrated with sufficient lot sucrose solution at 70° C. to achieve an ethanol weight percentage of 10.1 (12.5% v/v percent). The mixtures were stirred for one hour to form liposome suspensions.

The liposome suspensions were extruded through polycarbonate membranes to achieve a uniform size of 100 nm. The suspensions were then diafiltered against 10% sucrose solution to reduce the ethanol concentration to below 400 ppm. The suspensions were then ultrafiltered to above the target drug concentration, assayed for drug concentration and diluted to target by adding 10 mM histidine buffer and adjusting the pH to 6.5. The liposome size of each formulation was determined by Quasi-elastic light scattering and the particle size as a function of weight percent dpIUdR is shown in Table 1.

Example 3

Liposome Preparation According to Method of the Invention

The lipids hydrogenated soy phosphatidyl choline (HSPC) and distearoylphosphatidylcholine derivatized with methoxy-polyethyleneglycol (DSPE-mPEG) and dpIUdR in molar ratio of 89/5/6 were dissolved in ethanol at 70° C. until complete dissolution was achieved (about 1 hour). This lipid stock solution, after diluting as necessary to maintain a fixed lipid concentration, was hydrated with a 10% sucrose solution at 70° C. to vary the ethanol concentration from 8-44 weight percent. Each of the liposome mixtures were stirred for one hour to form liposome suspensions. The liposome particle size of each mixture was determined using quasi-elastic light scattering and the results are shown in Table 2.

Example 4

Liposome Preparation at 16.5 Weight Percent Lipid Solvent

The lipids hydrogenated soy phosphatidyl choline (HSPC) and distearoylphosphatidylcholine derivatized with methoxy-polyethyleneglycol (DSPE-mPEG) and dpIUdR in a molar ratios of 89/5/6, 85/5/10, 80/5/15, 70/5/25 and 55/5/40 were dissolved in ethanol at 70° C. until complete dissolution was achieved (about 1 hour). The lipid mixtures were hydrated with sufficient 10% sucrose solution at 70° C. to achieve a 16.5 weight percentage ethanol content in the hydration mixture (20% (v/v) ethanol). The mixtures were stirred for one hour prior to extruding the mixtures according to the procedure described in Example 2 and measuring the liposome particle sizes by quasi-elastic light scattering. The results are shown in Table 3.

Although the invention has been described with respect to particular embodiments, it will be apparent to those skilled in the art that various changes and modifications can be made without departing from the invention.

What is claimed is:

1. A method for preparing a liposome composition including a radiosensitizer, comprising mixing in a lipid solvent (i) a vesicle-forming lipid; (ii) between 1–20 mole percent of a vesicle-forming lipid derivatized with a hydrophilic polymer chain, and (iii) a radiosensitizer derivatized with a lipid moiety linked to the radiosensitizer, said lipid-derivatized radiosensitizer added in an amount sufficient to provide a drug-to-lipid molar ratio of between about 0.06–0.67; and adding an amount of a second solvent selected (i) to achieve a lipid solvent amount greater than 10 weight percent and less than about 50 weight percent and (ii) to obtain a liposome size less than that obtained at another lipid solvent amount, said lipid solvent and said second solvent being miscible at the amount of second solvent.

2. The method of claim 1, wherein the lipid solvent is an alcohol.

3. The method of claim 2, wherein the lipid solvent is methanol, ethanol or butanol.

4. The method of claim 1, wherein the second solvent is water.

5. The method of claim 1, wherein the radiosensitizer is 5-iodo-2'deoxyuridine or 5-bromo-2'deoxyuridine.

6. The method of claim 5, wherein the lipid moiety is a fatty acid.

7. The method of claim 5, wherein the lipid moiety is a saturated fatty acid.

8. The method of claim 7, wherein the lipid moiety is selected from lauric acid, myristic acid, palmitic acid, stearic acid, arachidic acid, behenic acid and lignoceric acid.

9. The method of claim 1 wherein the radiosensitizer is 5-iodo-2'-deoxyuridine and the lipid moiety is palmitic acid.

10. The method of claim 1, wherein the radiosensitizer is derivatized with a second lipid moiety.

11. The method of claim 10, wherein the radiosensitizer is 5-iodo-2'-deoxyuridine and the lipid moieties are palmitic acid.

12. The method of claim 1, wherein the hydrophilic polymer chain is polyethyleneglycol.

13. A liposome composition for administration of a radiosensitizer, comprising liposomes comprised of (i) a vesicle-forming lipid; (ii) between 1–20 mole percent of a vesicle-forming lipid derivatized with a hydrophilic polymer chain, and (iii) a radiosensitizer derivatized with a lipid moiety linked to the radiosensitizer, said lipid-derivatized radiosensitizer added in an amount sufficient to provide a drug-to-lipid molar ratio of between about 0.06–0.67, said liposomes obtainable by (a) mixing components (i), (ii) and (iii) in a lipid solvent, and (b) adding a selected amount of a second solvent, said selected amount effective (i) to achieve a lipid solvent amount greater than 10 weight percent and less than about 50 weight percent and (ii) to obtain a liposome size smaller than that obtained a lipid solvent amount other than said selected amount, said lipid solvent and said second solvent being miscible at the selected amount of second solvent.

14. The composition of claim 13, wherein the radiosensitizer is 5-iodo-2'deoxyuridine or 5-bromo-2'deoxyuridine.

15. The composition of claim 14, wherein the lipid moiety is a fatty acid.

16. The composition of claim 14, wherein the lipid moiety is a saturated fatty acid.

17. The composition of claim 16, wherein the lipid moiety is selected from lauric acid, myristic acid, palmitic acid, stearic acid, arachidic acid, behenic acid and lignoceric acid.

18. The composition of claim 13, wherein the radiosensitizer is 5-iodo-2'-deoxyuridine and the lipid moiety is palmitic acid.

19. The composition of claim 13, wherein the radiosensitizer is derivatized with a second lipid moiety.

20. The composition of claim 19, wherein the radiosensitizer is 5-iodo-2'-deoxyuridine and the lipid moieties are palmitic acid.

21. The composition of claim 13, wherein the hydrophilic polymer chain is polyethyleneglycol.

* * * * *